United States Patent [19]
Strandberg

[11] Patent Number: 6,097,983
[45] Date of Patent: Aug. 1, 2000

[54] CARDIAC EVENT DETECTING SYSTEM FOR A HEART STIMULATOR

[75] Inventor: Hans Strandberg, Sundbyberg, Sweden

[73] Assignee: Pacesetter AB, Järfälla, Sweden

[21] Appl. No.: 09/192,301

[22] Filed: Nov. 17, 1998

[30] Foreign Application Priority Data

Nov. 24, 1997 [SE] Sweden .................................. 9704311

[51] Int. Cl.[7] .................................................. A61N 1/368
[52] U.S. Cl. .............................................. 607/9; 600/518
[58] Field of Search .......................... 607/9, 14; 600/509, 600/515, 518

[56] References Cited

U.S. PATENT DOCUMENTS

| 4,557,266 | 12/1985 | Schober | 600/515 |
|---|---|---|---|
| 4,905,708 | 3/1990 | Davies | 600/518 |
| 5,058,599 | 10/1991 | Andersen | 600/518 |
| 5,607,457 | 3/1997 | Schüller | 607/9 |

FOREIGN PATENT DOCUMENTS

| 0 596 319 | 5/1994 | European Pat. Off. . |
|---|---|---|
| 0 646 390 | 4/1995 | European Pat. Off. . |
| WO97/39681 | 10/1997 | WIPO . |

*Primary Examiner*—Kennedy Schaetzle
*Attorney, Agent, or Firm*—Hill & Simpson

[57] ABSTRACT

A cardiac event detecting system for an implantable heart stimulator intended to be connected to the heart of a patient through at least two unipolar electrode leads or at least one bipolar electrode lead having one electrode pole in the atrium and one electrode pole in the ventricle for sensing heart signals, has at least two signal channels for signals sensed between the two electrode poles and between one of the electrode poles and the stimulator capsule, respectively. Each signal channel has a signal processing stage. Decision logic compares the signals from the two signal channels with signal criteria for detecting the occurrence of a cardiac event. An A/D-convertor converts sampled values of the sensed heart signals into digital words for each signal channel. The decision logic is adapted for comparing the digital words and their differences with the criteria for determining the occurrence of a cardiac event.

27 Claims, 5 Drawing Sheets

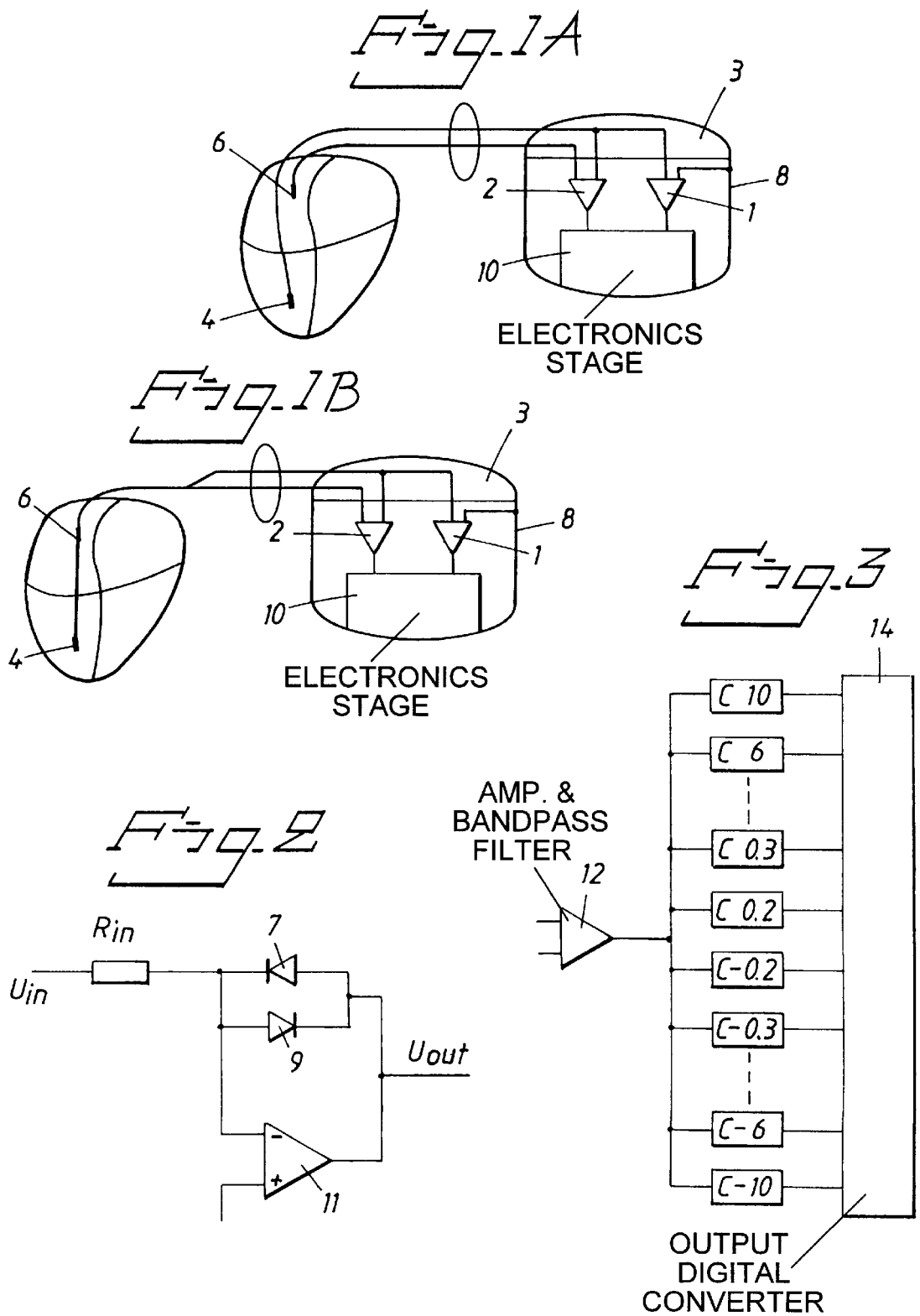

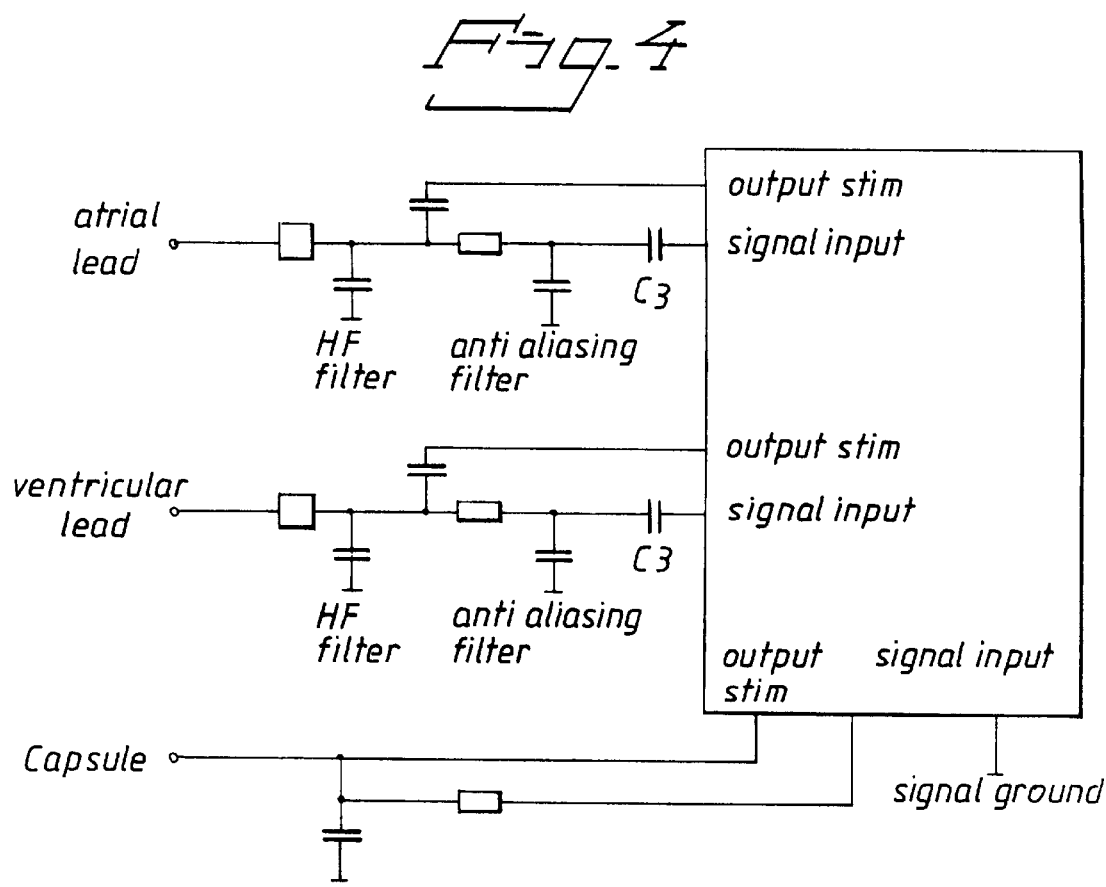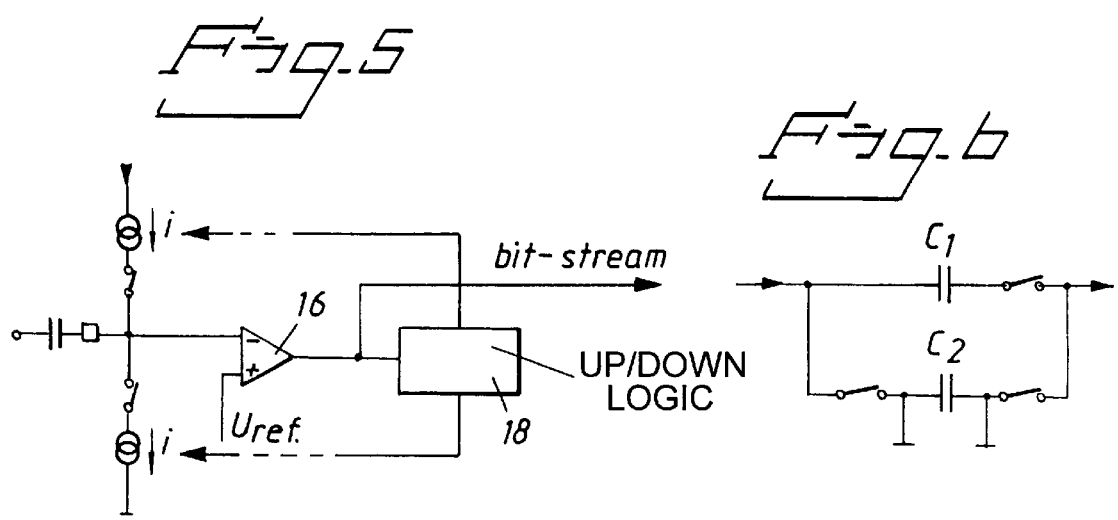

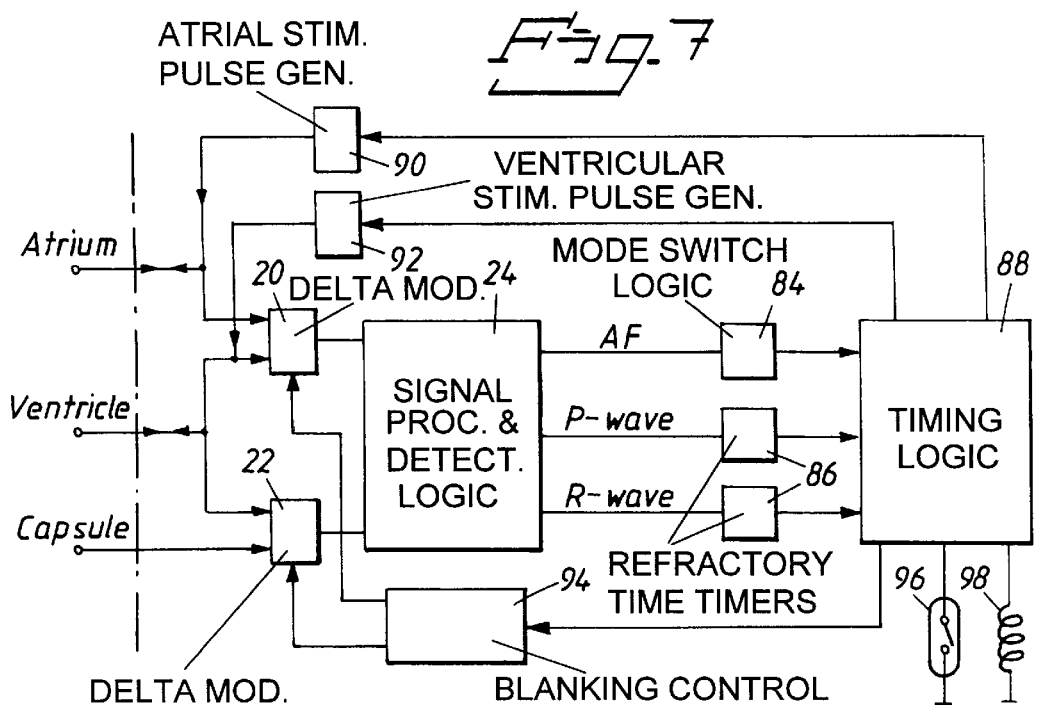
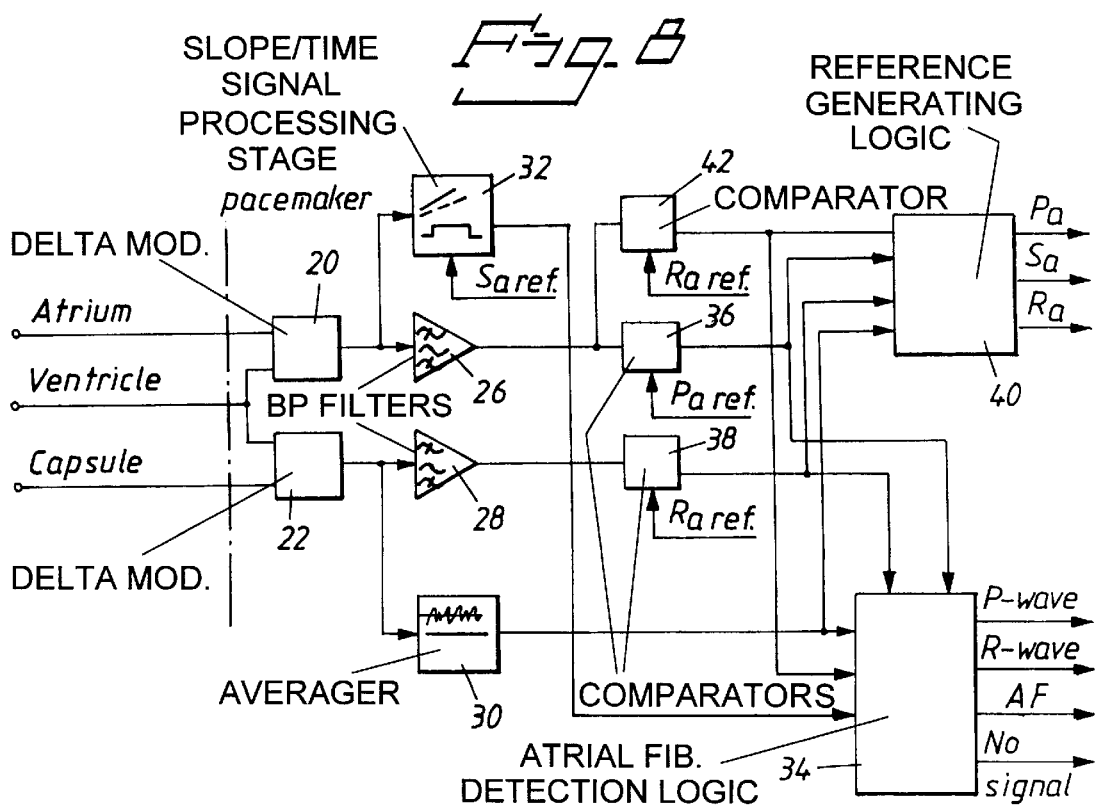

Table I

| channel 1 | channel 2 | similarity |
|---|---|---|
| 0 | 0 | 0 |
| 0 | 0 | 0 |
| 0 | 0 | 0 |
| 0 | 0 | 0 |
| 0 | 0 | 0 |
| -1 | 0 | 0 |
| -3 | 0 | 0 |
| -1 | 0 | 0 |
| 0 | 0 | 0 |
| 0 | 0 | 0 |
| 0 | 0 | 0 |
| 1 | 2 | 1 |
| 6 | 5 | 1 |
| 7 | 7 | 1 |
| 2 | 3 | 1 |
| -1 | -1 | 1 |
| 0 | 0 | 0 |
| 0 | 0 | 0 |
| 0 | 0 | 0 |
| 0 | 0 | 0 |
| 1 | 1 | 1 |
| 1 | 1 | 1 |
| 1 | 0 | 0 |

CARDIAC EVENT DETECTING SYSTEM FOR A HEART STIMULATOR

BACKGROUND OF THE INVENTION

1. Field of the Invention

The present invention relates to a cardiac event detecting system for an implantable heart stimulator intended to be connected to the heart of a patient with at least two unipolar electrode leads, or at least one bipolar electric lead having one electrode pole in the atrium and one electrode pole in the ventricle for sensing heart signals, the detecting system being of the type having at least two signal channels for signals sensed between the two electrode poles and between one of the electrode poles and the stimulator capsule respectively, each signal channel having a signal processing stage, and decision logic supplied with the respective channel signals for comparing the signals from the two signal channels with signal criteria for detecting the occurrence of a cardiac event.

2. Description of the Prior Art

In connection with cardiac pacing there is a general desire to be able to use unipolar electrodes instead of bipolar ones. Bipolar electrodes have two helically wound conductors connected to the electrode tip and ring respectively, which make the electrode more stiff and more frequently defective than a unipolar electrode, which only has one helically wound conductor.

In heart signal detection there are competing requirements. Thus a detecting level must be used for an absolutely reliable detection of the desired heart signals even at amplitude variations due to e.g. normal physiologically dependent amplitude variations, different heart signal origins, and possible variations in the electrode position. Further, a detecting level should be used for an absolutely reliable rejection of undesired signals, such as muscle interferences, far field heart signals and T-waves. A detecting level should also be used for most probable rejection of undesired external interferences. A reliable automatic adaption of the detecting level is also highly desirable.

A large number of different heart signal detectors are known. Normally these detectors include an amplifier with some kind of bandpass filter and a single signal amplitude comparator for determining whether a detection criterion is fulfilled. Certain types of adaption systems have a second "parallel" detector, but even in these latter systems the detection decision is made from a comparison in only one comparator.

Thus in U.S. Pat. No. 5,058,599 a method and an apparatus for detecting a sequence of abnormal events in the depolarization signal of a heart are described. A selective signal parameter is then compared to a defined threshold and the maximum value of the signal parameter is measured for each event which exceeds the threshold. The described method and apparatus are particularly well suited for detecting a sequence of events indicating fibrillation.

Detection of electrical events in the heart by measurements between an electrode pole in the atrium, an electrode pole in the ventricle and the heart stimulator enclosure are also known, see e.g. U.S. Pat. No. 5,607,457, European Applications 0 596 319 and 0 646 390.

U.S. Pat. No. 5,607,457 discloses an evoked response detector with unipolar electrodes in the atrium and the ventricle. A differential detector is connected to the electrode leads and detects cardiac activity between the atrial electrode and ventricular electrode. A correlation detector is connected between the pacemaker housing and one of the atrial or ventricular electrodes to generate a correlation signal identifying whether the detected cardiac activity arose in the atrium or in the ventricle.

European Application 0 596 319 discloses a heart stimulator having an electrode system including at least one bipolar electrode with one pole positioned in the atrium and one pole in the ventricle, or at least two unipolar electrodes arranged in the atrium and the ventricle, respectively. Atrial activity is measured between the two poles of the bipolar electrode or between the two unipolar electrodes, and ventricular activity is measured between the ventricular pole or electrode and the stimulator housing.

Also European Application 0 646 390 describes measurement between an atrial electrode and a ventricular electrode and measurement between the ventricular electrode and the heart stimulator housing for detecting spontaneous and evoked heart responses. One atrial comparator and one ventricular comparator are provided for comparing measured signals with an atrial reference potential and a ventricular reference potential, respectively.

U.S. Pat. No. 4,905,708 discloses an apparatus for recognizing cardiac arrhythmias. Analog signals obtained by sensing at the heart or on the body of the patient are digitized and a first differentiation of the digitized signals is carried out. A gradient pattern detector compares the differentiated signals with normal differentiated signals detected during sinus rhythm. Differences between the differentiated signals are indicative of pathological tachycardia, the nature of which can be identified by comparison with pre-programmed signals of like type.

SUMMARY OF THE INVENTION

An object of the present invention is to provide a cardiac event detecting signal system for a heart stimulator, which makes a more reliable detection than conventional detectors.

This object is achieved in accordance with the principles of the present invention in an implantable heart stimulator having a stimulator capsule, a lead system including an atrial electrode and a ventricular electrode, a detecting system contained in the stimulator capsule for detecting cardiac events, the detecting system being connected to the lead system and to the stimulator capsule and having a first signal channel for detecting signals sensed between the atrial electrode and the ventricular electrode, and a second signal channel for detecting signals sensed between one of the atrial electrode and the ventricular electrode, and the stimulator capsule, an analog-to-digital converter for obtaining sampled values of the signals in each of the first and second channels and for converting the sampled values into digital words, and decision logic supplied with the digital words for forming differences between the digital words and for comparing the digital words and the differences to reference criteria for determining the occurrence of a cardiac event.

A number of combined function criteria are used for the detection decision. In the detecting system according to the invention several simultaneous parallel signal processings are performed and from a number of combined "individual" detections prevailing heart signal activity is identified. With the detecting system according to the invention it is also possible to distinguish between the occurrence of different cardiac events. Thus, by digital processing of the digital words obtained the following distinct cardiac events can be distinguished, namely a cardiac event in the atrium (P-wave), a cardiac event in the ventricle (R-waves), cardiac signals which shall be omitted, interference received on the stimulator capsule, and no cardiac activity. Each event has its own pattern or word and the detection process is formed of the procedure for deciding of occurrence of a specific event.

In an embodiment of the system according to the invention, the A/D converter is formed by a set of comparators provided in each one of the signal channels, each comparator having a specific reference level for comparing the sampled values of the sensed heart signals with the reference levels, and a digital converter is provided for presenting the result of the comparisons in the form of the digital words composed of a "0" or a "1" for each comparator, depending on whether the sampled signal value is above or below the reference level in question. By performing several multi-amplitude signal detections simultaneously in this way a quicker A/D conversion is obtained.

In another embodiment of the system according to the invention, adjacent reference levels of the comparators are separated logarithmically with 30–70%. Such an exponential distribution of the reference levels requires less digital bits when a specific resolution is required for low level signals, and the distribution gives a constant relative accuracy for different amplitude levels in the following decision process. For example, each level of the above mentioned exponential distribution can be described by three digital bits. The same resolution for low levels and the same dynamic range require five bits with a linear A/D conversion.

In another embodiment of the system according to the invention a reference value creation unit is provided to adaptively adjust the reference values of the comparators. Such an adaption process is of importance since the determination of the discrimination level for the lowest acceptable levels of R-waves and P-waves have to be related to the noise level. The adaptive adjustment process can be started by an external command, or can be performed at regular time intervals, or reference values can be continuously adapted as functions of sensed signals, or the adaptive adjustment process can be started in response to the detection of a significant change in the sensed signals.

In the detecting system according to the invention influence from external interference is eliminated to a greater extent than in known heart signal detecting systems. In the determination process related to a possible cardiac event or specific heart signal all electrode combinations, time relations of the measured signals and information about the signal shapes are used to distinguish the signal information.

DESCRIPTION OF THE DRAWINGS

FIG. 1A schematically illustrates a pacemaker with an atrial electrode and a ventricular electrode connected to the heart of a patient, with two unipolar leads.

FIG. 1B schematically illustrates a pacemaker with an atrial electrode and a ventricular electrode connected to the heart of a patient, using a single bipolar lead.

FIG. 2 shows the circuit of a logarithmic analog amplifier suitable for use in connection with the A/D conversion in the system according to the invention.

FIG. 3 shows a circuit used in the system according to the invention for generating digital words representing measured signals.

FIG. 4 shows the connections of an IC-component of a heart stimulator.

FIG. 5 shows an embodiment of an input stage of an A/D-converter in the form of a delta modulator used in the system according to the invention.

FIG. 6 shows the typical basic block used in a switched capacitor network for the realization of the system according to the invention.

FIG. 7 is a schematic overall view of a typical heart stimulator with the detecting system according to the invention.

FIG. 8 shows the circuitry of the signal processing and detection logic of FIG. 7 more in detail.

DESCRIPTION OF THE PREFERRED EMBODIMENTS

Figure 9:
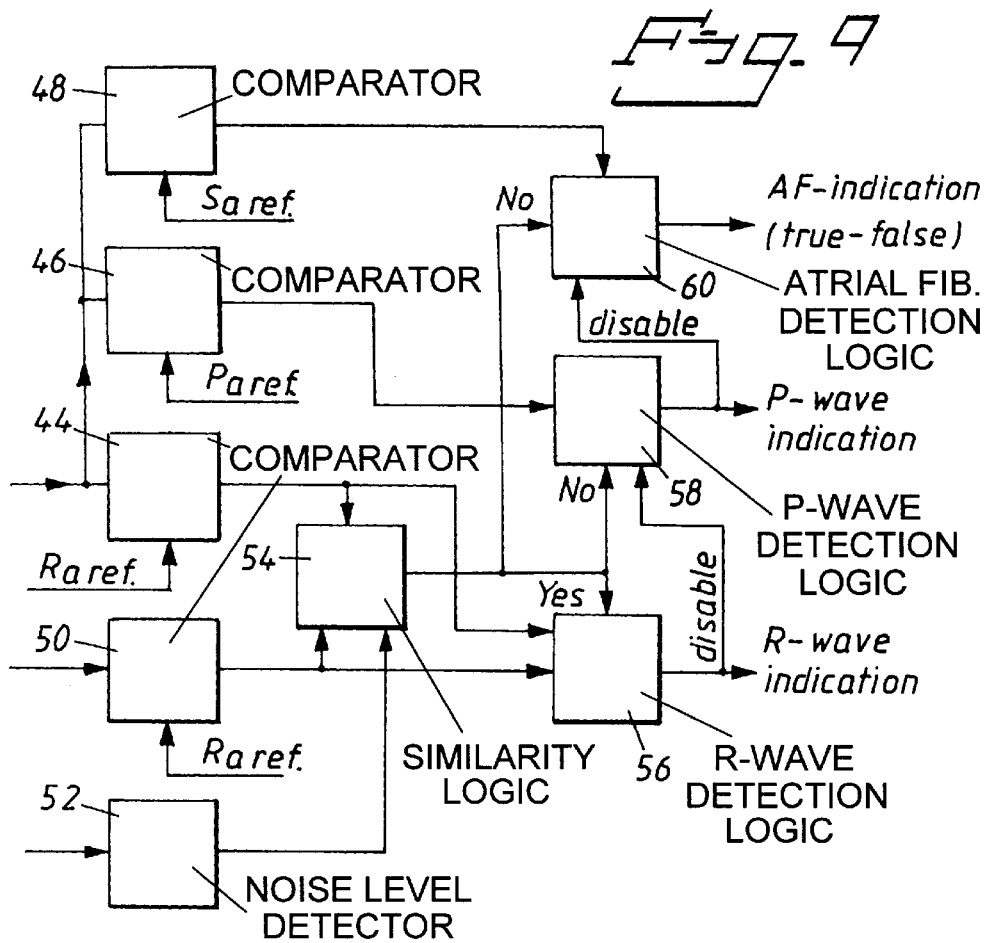
FIG. 9 shows a more detailed block diagram of the detection logic of FIG. 8.

The detecting system according to the invention is intended to be used in a heart stimulator with two unipolar leads 5A providing at least one unipolar electrode 4 in the ventricle and one unipolar electrode 6 in the atrium, as in FIG. 1A. In addition thereto the capsule 8 of the heart stimulator 3 is used as one electrode.

Instead of two unipolar electrodes a bipolar lead 5B can be used having one electrode pole 6 in the atrium and one pole in the ventricle 4 (FIG. 1B).

The detecting system according to the invention can also be used in a heart stimulator with at least two electrodes in the same heart chamber, provided that the electrodes are separated by a distance of sufficient length.

The detecting system according to the invention has electronics for signal processing in several steps, as will be described in more detail below. The electronics include at least two amplifiers 1 and 2 in FIGS. 1A and 1B, and passband and slew-rate filters with predetermined properties.

The amplifiers 1 and 2 are connected in two signal channels, which will be referred to below as channel 1 and channel 2, respectively. Thus the input of the amplifier 1 is connected to the ventricular electrode 4 and the stimulator capsule 8 and the amplifier 2 is connected across the ventricular electrode 4 and the atrial electrode 6.

The electronics stage 10 of the heart stimulator 3 in FIGS. 1A and 1B contains the rest of the electronics of the heart stimulator 3, such as comparators, digital signal processing components, stimulation pulse generators, etc.

For A/D-converting the measured analog signals, different A/D-converting techniques which are known can be used. Thus an A/D-converter with successive approximations can be used, i.e. a procedure of iterative digital up/down counting until the digital value corresponds to the analog input signal.

Alternatively, an A/D-converter in the form of a slope converter can be used. In such a converter the measured analog signal charges a capacitor for a predetermined time, determined as a predetermined number of clock pulses. The resulting voltage on the capacitor will then be proportional to the analog signal. In the next step the analog signal is disconnected and the capacitor is discharged to a known load. The discharge time is measured by counting clock pulses. Thus the count corresponds to the value of the analog signal.

Also, so-called delta/sigma converters can be used. The measured analog signal is compared with reference levels which are successively changed up or down by 1 bit until the level of the analog signal is reached. An average of a number of up/down counts gives the A/D-converted value.

So-called flash converters are preferred in the system according to the invention. These converters have a large number of parallel comparators to which the analog signal is supplied for simultaneous comparison in all the comparators. All the comparators are switched simultaneously according to the result of the comparison and the corresponding digital word is directly obtained.

In the above mentioned A/D-converters, the conversion can be "linear", i.e. a "linear" analog input signal is supplied to an A/D-converter in which linear steps are used in counting and comparing procedures. It can be an advantage, however, to transform the measured analog signal into a "logarithmic" signal before the A/D-conversion. For this transformation into a logarithmic form a logarithmic analog amplifier of the kind shown in FIG. 2 can be used. The input signal $U_{in}$ is supplied through a resistor $R_{in}$, to a circuit having two anti-parallel connected diodes 7, 9 forming a feedback loop for the amplifier 11. At the output of this circuit an output signal $U_{out}$ is produced related to the input signal $U_{in}$ as follows:

For $U_{in}>0$ $U_{out}=-\log|U_{in}|$ $U_{in}<0$ $U_{out}=+\log|U_{in}|$ $U_{in}=0$ $U_{out}=0$ A direct logarithmic conversion can be performed in a flash converter if the reference values of the comparators are logarithmically separated.

An embodiment of such a flash converter will be described below with reference to FIG. 3.

FIG. 3 shows an example of a circuit contained in the electronic stage 10 in FIGS. 1A and 1B for converting measured analog signals into digital words. The measured or sampled signals are supplied to a set of comparators C10, C6 . . . C0.3, C0.2, C−0.2, C−0.3 . . . C−6, C−10 through an amplifier and bandpass filter 12. In the comparators C10 . . . C−10 the input signals are compared with different reference levels. These reference levels can typically range from 0.2 mV to 10 mV with a logarithmic spacing of 30–70% between neighboring comparators. Both positive and negative reference levels are used.

The binary output signals from the set of parallel working comparators C10 . . . C−10 produce at an output digital converter 14 two digital words or patterns representing a sample of the signals measured in the two signal channels defined in FIGS. 1A and 1B.

The digital words received from the comparators C10 . . . C−10 can be either continuously processed in following detecting stages as soon as they are produced, or they can be sampled according to a predetermined time sequence and stored as a number of digital words and these stored digital words thus can be used in the subsequent detecting procedure.

Thus, the input signal is compared to the reference level of each of the comparators C10 , . . . C−10 and a "1" is obtained from those comparators where the input signal exceeds the reference level. From the other comparators the output signals are "0". The output signals from the comparators consequently give a set of "1" and "0" representing the input signal at a given time, e.g. 00111111, which indicates that the two comparators with the highest reference levels give "0" as output signals and the rest of the comparators give "1". This sequence of "0" and "1" is then translated into the digital number 0110 (=6) which forms the word in question. A sequence of words will in this way be generated representing the signals from the two signal channels as mentioned above and also the difference between the words is formed. These three sequences are compared with criteria for occurrence of a P-wave, an R-wave, muscle noise, etc. which makes the identification of a detected cardiac event more reliable.

For the occurrence of a R-wave the sequence of words from channel 1 in FIGS. 1A and 1B can typically be 0+2−5−6−20 and the sequence of words from channel 2 0+1−4−6−3−1.

The criteria for R-wave detection can be

Word 1 sequence <−2, <−4, <−1

Word 2 sequence <−2, <−4, <−1

Word 1 −word 2 sequence ±1, ±1, ±1.

All these conditions must be fulfilled for a detected cardiac event to be identified as an R-wave.

The criteria for P-wave detection could be

Word 1 sequence <+1, <+1, <+1

Word 2 sequence >+1, >+3, >+1

As appears from the above example, the word 1 and word 2 sequences of the R-wave detection criteria are similar, whereas there is a significant difference between the corresponding sequences of the P-wave detection criteria. This is due to the fact that the R-wave is much stronger than the P-wave. Thus the sensitivity of channel 1 which measures the signal between the ventricular electrode 4 and the stimulator capsule 8 can be adjusted such that only ventricular events are detected, whereas the sensitivity of channel 2 which measures the signal between the ventricular and the atrial electrodes 4 and 6 is adjusted such that both atrial and ventricular events are detected. Consequently for an R-wave the word 1 sequence and the word 2 sequence will be essentially equal, whereas for P-waves there is a significant difference between the word 1 sequence and the word 2 sequence, since a P-wave is only detected in channel 2. This circumstance is apparent from the example above.

For muscle noise the word sequence can typically be +2+10−2+1−10 and the muscle noise detection criteria can be Word 1 sequence >±1 or<−1

Word 2 sequence ≦+I and ≧−1.

A higher noise level is normally received in channel 1 which is connected to the stimulator capsule 8. No activity signals give low level words which can be considered as "noise" words. R- and P-waves give "higher level" words. These higher level words must be distinct and different from the noise level words to give detectability. By utilizing the fact that noise appears substantially only in that signal channel which is connected to the stimulator capsule 8, an automatic change of the R-wave and P-wave discriminating levels, when muscle noise appears, can be provided. This change of discriminating levels is an adaptation process such that the lowest acceptable levels of R-wave detection and P-wave detection respectively together with the noise level will determine the discrimination level. The detecting system according to the invention is consequently provided with an automatic sensing threshold setting function.

As mentioned above, according to one example of the detecting system according to the invention five distinct cardiac events in this way can be distinguished by digital signal processing of the digital words received from the comparators C10 . . . C−10. These cardiac events are a) occurrence of an atrial event (P-waves), b) occurrence of a ventricular event (R-waves), c) other cardiac signals which shall be omitted, d) interferences received on the heart stimulator capsule, and e) no cardiac activity. Each event has its own pattern or word and the detection process produces a decision as to the source of an identified event.

FIG. 4 shows the connections of an IC-component used in a heart stimulator provided with a detecting system according to the invention. Thus there are three connections for the atrial lead, the ventricular lead, and for connection to the stimulator capsule, respectively. The connections for the atrial lead and the ventricular lead are designed for both delivery of stimulation pulses, "output stim", and for receiving sensed signals, "signal input". Both connections are provided with a high frequency filter for removing radio frequency interferences etc. and an anti-aliasing-filter for removing frequencies above the sampling frequency which is employed. The sampling frequency is typically in the range of 20–2000 Hz, i.e. a number of samples are taken during a cardiac cycle. A capacitor $C_3$ is also provided in each connection for removing DC-components.

FIG. 5 shows an input stage to an A/D-converter in the form of a delta modulator, suitable for use in the detecting system according to the invention. Analog measurement signals are then converted into a digital bit stream by a comparison procedure conducted in a comparator 16, controlled by up/down logic 18.

FIG. 6 shows a basic block formed of capacitors $C_1$, $C_2$, and switches for switched capacitor networks. Networks of such blocks are suitable for use in the detecting system according to the invention for realizing such signal processing as bandpass filtering—a passband of 20–180 Hz is appropriate for the system according to the invention— signal integration, etc. The processing properties are determined by the relation between capacitor values in the basic blocks and the way of connecting the blocks. Thus, if, for example, the block is placed in a forward signal path, the signal processing properties will be different from the signal processing properties if the block were connected in a feedback path.

The construction of suitable switched capacitor networks is known and need not be described in more detail in this connection.

FIG. 7 shows a block diagram of a heart stimulator having a cardiac event detecting system according to the invention.

On the input side two delta modulators 20, 22 are provided for differentially processing the signals between the atrial and ventricular electrodes and between the ventricular electrode and the stimulator capsule, respectively. As an alternative the delta modulator 22 can be connected to a signal channel formed of the atrial electrode and the capsule.

The delta modulators 20, 22 are connected to a signal processing and detection logic 24 with a bandpass filter 26, 28 in each signal half, cf. FIG. 8.

On the output side of the signal processing and detection logic 24 of the heart stimulator in FIG. 7 a mode switch logic 84 is connected, which is activated in case of the detection of atrial fibrillation. Two refractory time, timer 86 introduces a refractory time into the pacemaker timing logic 88 in response to the detection of a P-wave and an R-wave respectively. The heart stimulator also has an atrial stimulation pulse generator, 90 and a ventricular stimulation pulse generator 92 controlled by the pacemaker timing logic 88. A blanking control 94 is further connected between the pacemaker timing logic 88 and the delta modulators 20, 22 for preventing inappropriate detection of signals during a blanking period starting with the delivery of a stimulation pulse.

A reed-element 96 and telemetry communication circuitry 98 are connected to the pacemaker timing logic 88 for making external control of the heart stimulator possible.

The signal channel connected to the stimulator capsule 8 may also pick up external interference signals, such as muscle noise, as discussed above. For determining the noise level the signal processing and detection logic 24 includes a signal averager 30, see FIG. 8, in which rectified average values of the noise signals is formed in an averaging process.

In the averager 30 the noise level can be determined as the average signal during a specific time, for example during one second. The average value can be determined by the use of a counter adding the A/D-converted binary values, without the sign, e.g. for each millisecond. The average noise level value is then 1/1000 of the counter value.

Alternatively the averager 30 can be a digital recursive filter for producing a running average value. The determined noise level is used in an adaptation process to change the reference values for the detection of different cardiac events. This process takes place in the reference generating logic 40.

When there is a signal level above zero on that signal path which is connected to the stimulator capsule 8, preferably no signal is added to the noise averaging process in the averager 30.

The output of the delta modulator 20 which is connected to the signal channel containing the atrial electrode is also supplied to a signal processing stage 32 which may be a part of the signal processing and detection logic 24. The signal processing stage 32 is devised for slope/time processing of the output signal from the delta modulator 20 and comparison with a reference value $S_{aref}$. The signal processing stage 32 is connected to detection logic 34 for determining whether atrial fibrillation, AF, is present. Thus, in the slope/time processing stage 32 it is determined whether the slope of the signal exceeds a predetermined time and, if this condition is fulfilled for a period of time, it is also determined whether this exceeds a predetermined time limit. If both of these conditions are fulfilled, the existence of atrial fibrillation is determined in the detection logic 34. If P-waves are detected the slope time processing stage 32 is disconnected.

The two signal processing chains 20, 26 and 22, 28 could be realized with very different techniques, but the processing result will be the same. One technique is to digitize the signal in connection with the input, and then all filtering and detection are performed in computing processes.

Another way is to use analog components and filter, and then perform the digitizing at the comparator stage.

A preferred solution is the previously mentioned switched capacitor technique. Even if the signal is sampled, the signal processing is in reality analog.

After analog signal processing an A/D signal converter is provided in each single channel for converting the analog measurement signals into values of amplitude and sign. Also this A/D conversion can be realized with the aid of a switched capacitor network. A suitable solution is to use a set of amplitude comparators in the switched capacitor network of the kind described above in connection with FIG. 3. These sets of comparators are represented by the blocks 36 and 38 respectively in FIG. 8. The reference levels of the comparators can be, as described in connection with FIG. 3, accurately determined in an easy way by choosing suitable relative capacitor values in the network. The levels of the comparators preferably are selected as an exponential sequence, e.g. 0, 0.50, 0.77, 1.2, 1.8, 2.8, 4.3, and 6.5 mV and with both positive and negative levels. By such an exponential distribution of the reference levels two advantages are obtained, namely a lower number of digital bits for a specific resolution for low signal levels, and a constant relative accuracy for different amplitude levels in the following decision process. Each level of the above exponential distribution can be described by three digital bits. To get the same resolution for low levels and the same dynamic range, five bits are required with a linear A/D-conversion.

When using higher resolution, the advantage with fewer bits for the logarithmic solution, compared to the linear, is even better.

A comparator 42 is also arranged in the signal channel connected to the atrial and ventricular electrodes for comparing the signal on this channel with the reference value $R_{aref}$ for detection of R-waves, since both P-waves and R-waves appear in the signal in this channel.

In the decision logic 34 the processed signals from the two signal paths comprising the atrial and ventricular electrode and the ventricular electrodes and the stimulator capsule, respectively, are compared to reference values $R_{aref}$ for R-waves, $P_{aref}$ for P-waves and $S_{aref}$ for the slope of the signal for atrial fibrillation detection, the reference values being produced by the adaptive process described above. The signal in the channel comprising the atrial and ventricular electrodes is compared in the comparators 44, 46, 48 with respective reference values $R_{aref}$, $P_{aref}$ and $S_{aref}$ for R-wave, P-wave, and atrial fibrillation (see FIG. 9 which shows the decision logic 34 in FIG. 8 in more detail). The signal in the other signal channel comprising the ventricular electrode and stimulator capsule is compared in the comparator 50 with the reference value $R_{aref}$ for R-wave and this signal is also supplied to a noise level detector 52 for determining the noise level as described above. In a similarity logic 54 the signals from the two channels are compared. In this comparison process the noise level is considered as well The output signals from the comparators 44, 46, 48, 50 and from the similarity logic 54 are supplied to an R-wave logic 56, a P-wave logic 58 and an AF detecting logic 60, in which R-wave, P-wave and AF indications are decided.

A rate check is also performed in the decision logics 56, 58, 60.

There are four states which have to be distinguished by the decision logics 56, 58, 60 in FIG. 9, namely 1) P-wave, 2) R-wave, 3) atrial fibrillation, and 4) no signal.

From the sensed data it shall be decided which of the above four events takes place at each time.

If a similarity between the signals on the two channels is detected by the similarity logic 54, a detected event must be an R-wave since R-waves appear on both channels as discussed above. When an R-wave is detected the P-wave logic 58 is disabled.

In case of non-similarity between the signals on the two channels detected by the similarity logic 54 a detected cardiac event is decided to be a P-wave or atrial fibrillation. In case of detecting a P-wave in the P-wave logic 58 the AF detecting logic 60 is disabled.

In the decision process time relations between the occurrence of different cardiac events are also considered. For example, an R-wave cannot appear within 280 msec from the previous R-wave. A P-wave cannot appear within 280 msec from the previous P-wave. An atrial fibrillation shall appear within 150–400 msec from the previous one and the shape criteria of the fibrillation signal shall be within maximum and minimum slope criteria and within maximum and minimum slope duration. Thus also such time relations are considered in the decision logics 56, 58, 60.

Figure 10:
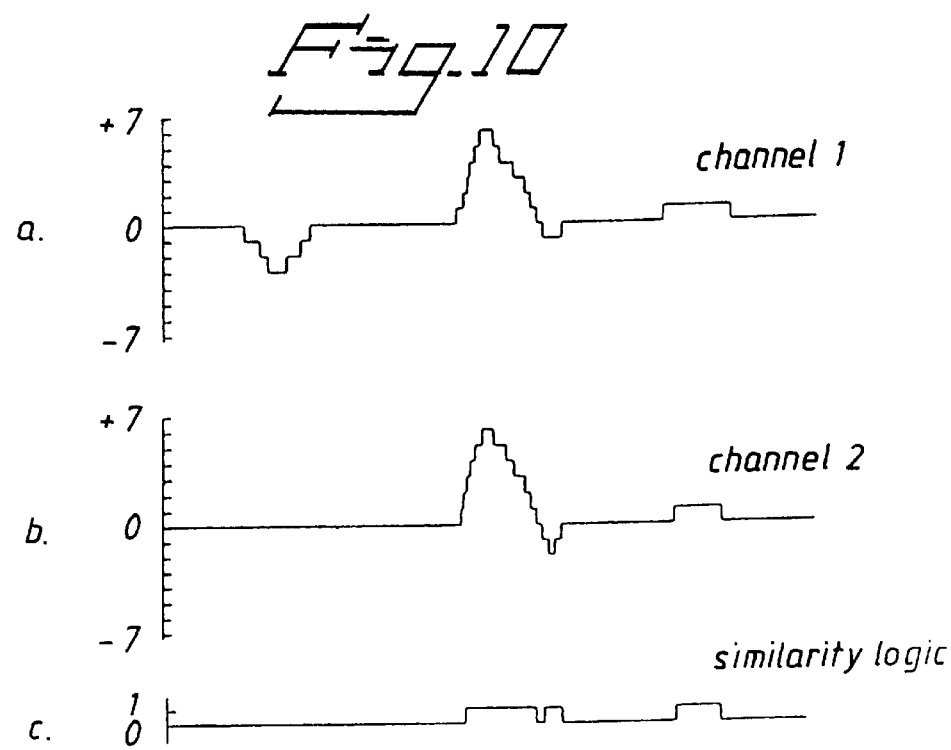
FIG. 10 shows an example of the signals on the two signal channels and the output signal from a similarity logic as functions of time.
Figures 11, 12:
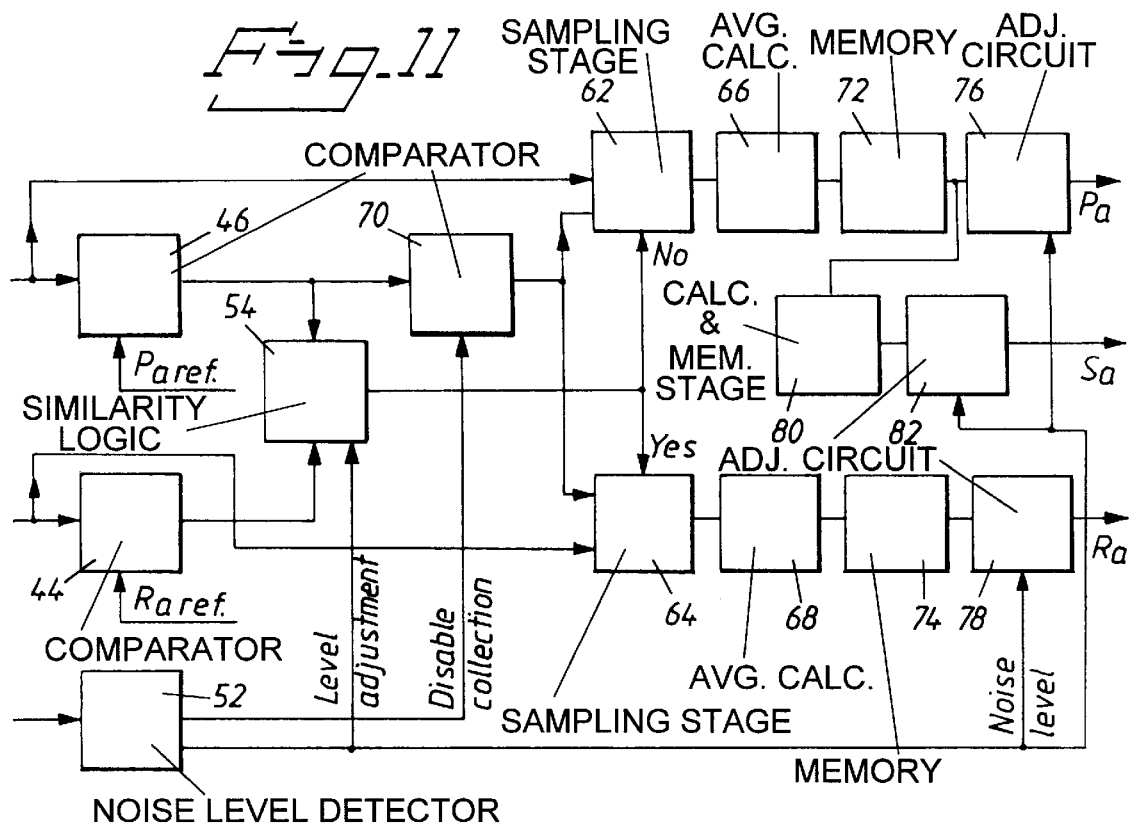
FIG. 11 shows the circuitry of the reference creation logic of FIG. 8 in more detail.
FIG. 12 is a table illustrating processed signals sampled in time with equal time partition.

The processed signals can either be digital in amplitude and analog in time as shown in FIGS. 10a and 10b or sampled in time with equal time partition as illustrated in the table shown in FIG. 12.

In FIGS. 10a, 10b and 10c channel 1 shows the signal sensed between the atrial and ventricular electrode and channel 2 shows the signal between the ventricular electrode and the stimulator capsule. The P-wave appears in the signal on channel 1 but not on the signal on channel 2 whereas the R-wave appears in the signals on both channels. FIG. 10c shows the output signal from the similarity logic 54 comparing the similarity of the signals from the two channels.

A detected cardiac event is a P-wave when the following criteria are satisfied:

Channel 1 (value)$\geq P_{aref}$

Channel 1 (sign)=sign($P_{aref}$)

Channel 2 (value)$< R_{aref}$

Channel 2 (sign)=any

Similarity=0.

A cardiac event is decided as an R-wave if the following criteria are satisfied:

Channel 1 (value)=any

Channel 1 (sign)=any

Channel 2 (value)$\geq R_{aref}$

Channel 2 (sign)=sign($R_{aref}$)

Similarity=1

More complex decision criteria can include the satisfaction of a certain time sequence. For accepting a detected cardiac event as a P-wave each value relation above shall be fulfilled at three times, i.e.

Channel 1 (value 1)$\geq P_{aref1}$

Channel 1 (sign 1)=sign($P_{aref1}$)

Channel 2 (value 1)$< R_{aref(max)}$

Channel 1 (value 2)$\geq P_{aref2}$

Channel 1 (sign 2)=sign($P_{aref2}$)

Channel 2 (value 2)$< R_{aref(max)}$

Channel 1 (value 3)$\geq P_{aref3}$

Channel 1 (sign 3)=sign($P_{aref3}$)

Channel 2 (value 3)$< R_{aref(max)}$

At least one similarity data at the maximum of the stored P (value)=0.

The reference values $R_{aref}$, $P_{aref}$, and $S_{aref}$ and possible other reference values depending on the complexity of the decision process are stored. These reference values are created from the acquired signal data and are successively updated.

The calculation of the reference values are performed in the reference creation logic 40 in FIG. 8 and updating the reference value can take place e.g. by external order, through telemetry control, on a regular basis in the heart stimulator, continuously from a start time, in case of a significant change in the statistical processing of input data. The reference creation logic is shown in greater detail in FIG. 11. The collecting of values for statistical or average calculations in the detecting system according to the invention are performed according to specified criteria.

If the signal on the channel comprising the atrial and ventricular electrodes has a value $> P_{aref}$, determined in the comparator 46, a new value is expected and the maximum value is collected by peak signal sampling stage 62, 64, see FIG. 11. Similarity between the two channels is recorded by the similarity logic 54 and the time from previous collected data with the same type of similarity is checked to be within the time criteria. If the similarity and the sign are satisfied for a P-wave or an R-wave the value is transferred to average calculators 66, 68 or to circuits for performing other statistical processes.

If there is an interference level above a specified threshold value on the channel connected to the stimulator capsule this is determined by the noise level detector 52. No collecting and updating of the reference values are then performed. Thus in this case the noise level detector 52 disables the collection of signal data by means of a comparator 70 in which the measured noise level is compared to the predetermined acceptable maximum threshold value.

If a more complex detection or decision process with time sequences is used additional data are used for the average process. Values also before and after the maximum value are then used and coordinated with the respective reference time for the average determining process. For example if $P_{a2}$ is the measured maximum value, $P_{a3}$ is a value measured 4 msec before the maximum and $P_{a3}$ the value measured 4 msec after the maximum value also average values of $P_{a1}$ and $P_{a3}$ are calculated. These average values may e.g. be calculated for that last 16 values.

The average values can also be determined by recursive filtering. New values are then always added and $\frac{1}{256}$ of the actual sum is subtracted. The sum shifted by 8 bits, which is equal to division by 256, is then used as the average heart signal amplitude.

The calculated average values $P_a$ and $R_a$ are stored in memories 72, 74 together with their signs and adjustment circuits 76, 78 are connected to these memories 72, 74 for momentary adjustment of $P_a$ and $R_a$, respectively.

The noise level detector 52 is connected to the adjustment circuits 78 for inhibiting the momentary adjustment of $R_a$, if the noise level exceeds the allowed maximum threshold value, as discussed above.

The reference generating logic 40 also includes a calculation and memory stage 80 for calculating the average value $S_a$ of the specific signal slope for use in connection with the detection of atrial fibrillation from the signals on the channel having the atrial and ventricular electrodes. An adjustment circuit 82 is also provided for momentary adjustment of the existing reference value $S_{aref}$ by the last calculated and stored $S_a$ to update $S_{aref}$.

Also the adjustment circuits 76, 82 for $P_a$ and $S_a$ respectively are connected to the noise level meter 52 for inhibition of the updating process when the noise level exceeds the maximum allowed threshold value.

For many applications the adjustment circuits 76, 82 for $P_a$ and $S_a$ is not needed and can be omitted.

An interference adjustment of the $S_{aref}$ is not needed if a combipolar connection or a bipolar atrial electrode is used for the atrial fibrillation detection.

The determined reference values $P_{aref}$ and $R_{aref}$ are used in comparators for comparing the processed input signals with these reference values in the decision process, as described above. The values $P_{aref}$ and $R_{aref}$ can be e.g. 2 steps below the corresponding average values and the limits $P_{aref}$ and $R_{aref}$ for detection of a P-wave and an R-wave respectively can be at least two steps above the determined average noise level. This means that $P_{aref}$ or $R_{aref}$ can be momentarily adjusted in a noisy situation by one step to avoid false detections due to noise while still having a high probability of heart signal detection. However, adjustment by two steps cannot be allowed. Instead a too noisy situation then has to be indicated and the heart stimulator is controlled to stimulate the patient's heart asynchronously with an interference rate.

For the detection of atrial fibrillation separate signal processing takes place for determining the specific heart signal morphology and rate. The fibrillation signals may have an amplitude of the same order or magnitude as P-waves but are often much lower. Further the slopes of the signals are often lower than those of normal heart signals and the signal intervals are often irregular and shorter than 400 msec but longer than 150 msec. A suitable signal processing can comprise e.g. a signal slope follower, at unit 48 in FIG. 8, and information about the signal slope is combined with a signal duration criterion in the AF detection logic 60 for determining whether atrial fibrillation exists or not. As long as normal P-waves are detected there is no need to check possible occurrence of atrial fibrillation. In the absence of detected P-waves, the atrial fibrillation function of the detecting system according to the invention is activated. The amplitude criteria is determined with the aid of a reference value $S_{aref}$. This reference value can be based on the reference value $P_{aref}$. If a signal duration is fixed to e.g. 8 msec the $P_a$ value can be used to calculate the slope criterion. The slope reference value $S_{aref}$ can be calculated as a certain percentage, e.g. 50% of $P_a \times 1000/8 \approx 50\%$ of $P_a \times 128$. Thus the reference value $S_{aref} = P_a \times 64$ which is easily calculated by shifting a binary data 6 bits if the $P_a$ value exists in linear binary form.

The detecting system according to the invention exhibits several advantages from a constructional point of view. Thus amplifiers and filters can be conventionally designed. Programming circuitry and registers for the detection are omitted which saves space. Comparators can be designed with relatively small surface compared with the amplifiers. If the analogue signal is processed in a switched capacitor network the comparators and the comparator reference levels are easily built in as parts of the switched capacitor network with very low extra space requirements. The digital logic required for the processing of the digital words as described above requires some space in the integrated circuit forming the detecting system, but requirements of digital logics are very small compared to requirements for analogue processing in this regard.

The decision making functions of the detecting system according to the invention are realized by digital technique.

The A/D-conversion can be performed at different stages of the signal processing. Therefore, as an alternative to the above described embodiments comprising two delta modulators, A/D-converters can be provided at the input side of the detecting system for creating amplitude values with enough resolution. Ordinary digital signal processing is then performed instead of signal processing with the aid of switched capacitor networks.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable heart stimulator comprising:
   a stimulator capsule;
   a lead system including an atrial electrode adapted for placement in an atrium and a ventricular electrode adapted for placement in a ventricle;
   a detecting system contained in said stimulator capsule for detecting cardiac events, said detecting system being connected to said lead system and to said stimulator capsule and having a first signal channel for detecting signals sensed between said atrial electrode and said ventricular electrode, and a second signal channel for detecting signals sensed between one of said atrial electrode and said ventricular electrode, and said stimulator capsule;
   an analog-to-digital converter for obtaining sampled values of said signals in each of said first and second channels and for converting said sampled values into digital words; and decision logic applied with said digital words for forming differences between said digital words and for comparing said digital words and said differences to reference criteria for determining an occurrence of a cardiac event.

2. An implantable heart stimulator as claimed in claim 1 wherein said analog-to-digital converter comprises a first set of comparators in said first channel and a second set of comparators in said second channel, each comparator in each of said first and second sets having a reference level respectively associated therewith and each comparator comparing said sample values of said signals to the respective reference level and generating a comparison result as one of a low logic level or a high logic level depending on whether a sampled value is above or below the respective reference level, and a digital converter, supplied with the respective comparison results from all of the comparators in each of said first and second sets for combining said comparison results as said digital words.

3. An implantable heart stimulator as claimed in claim 2 wherein the respective comparators in said first set are separated logarithmically from each other in a range between 30% and 70%, and wherein the respective comparators in said second set are separated logarithmically from each other in a range between 30% and 70%.

4. An implantable heart stimulator as claimed in claim 2 wherein said first set of comparators includes respective comparators having a positive reference level and respective comparators having a negative reference level, and wherein said second set of comparators includes respective comparators having a positive reference level and respective comparators having a negative reference level.

5. An implantable heart stimulator as claimed in claim 2 further comprising a reference value generator connected to each of the comparators in said first set and each of the comparators in said second set for adaptively adjusting the respective reference values of all of said comparators.

6. An implantable heart stimulator as claimed in claim 5 further comprising a telemetric receiver disposed in said stimulator capsule for telemetrically receiving externally-originating commands, including a command to start an adaptive adjustment process, and wherein said telemetry receiver is connected to said reference value generator for activating said reference value generator upon receipt of said command to start an adaptive adjustment process.

7. An implantable heart stimulator as claimed in claim 5 further comprising means for periodically activating said reference value generator to adaptively adjust the respective reference values of all of said comparators at regular time intervals.

8. An implantable heart stimulator as claimed in claim 5 wherein said reference value generator continuously adapts said respective reference values of all of said comparators dependent on said signals in said first and second channels.

9. An implantable heart stimulator as claimed in claim 5 wherein said reference value generator is activatable to start an adaptive adjustment process in response to a detection of a change of a predetermined amount in the respective signal in at least one of said first channel and said second channel.

10. An implantable heart stimulator as claimed in claim 5 wherein said reference value generator comprises an average value calculator, including a counter, for adding binary signal values representing at least one of the defected signal in said first channel and the defected signal in said second channel, without an operational sign, for determining an average value during a predetermined time of said at least one of said signal in said first channel and said signal in said second channel.

11. An implantable heart stimulator as claimed in claim 10 wherein said average value calculator comprises a digital recursive filter for producing a running signal average value.

12. An implantable heart stimulator as claimed in claim 10 further comprising means for activating said average value calculator to operate at predetermined times.

13. An implantable heart stimulator as claimed in claim 5 further comprising a noise level detector supplied with said signal in said second channel for detecting a noise level in said signal in said second channel, and connected to said reference value generator for inhibiting said reference value generator if said noise level exceeds a predetermined level.

14. An implantable heart stimulator as claimed in claim 13 further comprising an averaging unit connected preceding said noise level detector for averaging said signal in said second channel to obtain an average value of said signal in said second channel which is supplied to said noise level detector.

15. An implantable heart stimulator as claimed in claim 1 further comprising a delta modulator connected in each of said first channel and said second channel preceding said analog-to-digital converter.

16. An implantable heart stimulator as claimed in claim 1 wherein said decision logic is continuously supplied with said digital words for comparison with said reference criteria.

17. An implantable heart stimulator as claimed in claim 1 further comprising a memory supplied with a sequence of said digital words for storing said sequence of digital words and for supplying said digital words in said sequence to said decision logic, said decision logic comparing said sequence of digital words with said reference criteria.

18. An implantable heart stimulator as claimed in claim 1 further comprising a memory for storing said digital words, and wherein said decision logic comprises a sampling unit for sampling the digital word stored in said memory at successive times to obtain sampled words, and said decision logic comparing said sampled words with said reference criteria.

19. An implantable heart stimulator as claimed in claim 1 wherein said decision logic comprises similarity logic for comparing respective digital words from said first and second channels to determine a mutual signal similarity between said digital words respectively from said first and second channels.

20. An implantable heart stimulator as claimed in claim 1 further comprising a slope/time processor connected in said first channel, and an atrial fibrillation detector connected to an output of said slope/time processor for comparing the output of said slope/time processor to signal criteria indicative of atrial fibrillation for identifying an occurrence of atrial fibrillation.

21. An implantable heart stimulator as claimed in claim 20 wherein said atrial fibrillation detector is inhibited upon an occurrence of a P-wave in said signal in said first channel.

22. An implantable heart stimulator as claimed in claim 1 further comprising, in each of said first and second channels, a band-pass filter having a pass band between 20 Hz and 180 Hz.

23. An implantable heart stimulator as claimed in claim 1 further comprising, in each of said first and second channels, a slew rate filter.

24. An implantable heart stimulator as claimed in claim 1 further comprising, in each of said first and second channels, a signal processor, and wherein said analog-to-digital converter and said signal processor comprise switched capacitor networks.

25. An implantable heart stimulator as claimed in claim 1 wherein said decision logic comprises means for receiving signals from a plurality of different electrode combinations for discriminating signal information for determining cardiac events by comparing said signals to a plurality of different reference criteria.

26. An implantable heart stimulator as claimed in claim 1 wherein said lead system comprises a bipolar lead carrying said atrial electrode and said ventricular electrode.

27. An implantable heart stimulator as claimed in claim 1 wherein said lead system comprises a first unipolar lead carrying said atrial electrode and a second unipolar lead carrying said ventricular electrode.

* * * * *